United States Patent
Papuashvili

(12) 
(10) Patent No.: US 6,242,197 B1
(45) Date of Patent: Jun. 5, 2001

(54) USE OF URINARY TRYPSIN INHIBITOR FOR THE DIAGNOSIS OF THE ONSET OF AIDS

(75) Inventor: Marina N. Papuashvili, Moscow (RU)

(73) Assignee: Technologie Integrale Limited (GB)

( * ) Notice: Subject to any disclaimer, the term of this patent is extended or adjusted under 35 U.S.C. 154(b) by 0 days.

(21) Appl. No.: 09/487,690

(22) Filed: Jan. 19, 2000

(30) Foreign Application Priority Data

Jan. 26, 1999 (DE) ................................................ 199 03 034
May 5, 1999 (DE) ................................................ 199 20 704

(51) Int. Cl.[7] ............................. G01N 33/53; C12Q 1/00
(52) U.S. Cl. ................................. 435/7.1; 435/4; 435/975
(58) Field of Search .................................. 435/7.1, 4, 975

(56) References Cited

U.S. PATENT DOCUMENTS 5,504,065 * 4/1996 Hattori et al. ............................. 514/8

FOREIGN PATENT DOCUMENTS 0 371 706 A1  11/1989 (EP) .

OTHER PUBLICATIONS

Koito et al., "A Neutralizing Epitope of Human Immunodeficiency Virus Type 1 Has Homologous Amino Acid Sequences With Active Site of Inter–Alpha–Trypsin Inhibitor," *International Immunology*, 1(6):613–618(1989)(abstract only).

Kuwajima et al., "Automated Measurement of Trypsin Inhibitor in Urine with a Centrifugal Analyzer: Comparison with Other Acute Phase Reactants," *Clinical Biochemistry*, 23(2):167–171 (1990) (abstract only).

Kuwajima et al., "Urinary Tryspin Inhibitor as an Acute Phase Reactant," *Japanese Journal of Clinical Pathology*, 40(7):751–755 (1992) (abstract only).

Ogloblina et al., "Monoclonal Antibodies that Recognize Trypsin Binding Domain of Human Urinary Trypsin Inhibitor," *Hybridoma*, 12(6):745–754 (1993) (abstract only).

* cited by examiner

*Primary Examiner*—Louise Leary
(74) *Attorney, Agent, or Firm*—Nixon Peabody LLP

(57) ABSTRACT

The present invention pertains to the use of urinary trypsin inhibitor for the diagnosis of the onset of AIDS and to a kit for performing such an assay. The present invention also relates to the use of urinary trypsin inhibitor for testing the efficacy of anti-HIV drugs.

18 Claims, 1 Drawing Sheet

USE OF URINARY TRYPSIN INHIBITOR FOR THE DIAGNOSIS OF THE ONSET OF AIDS

Figure 1:
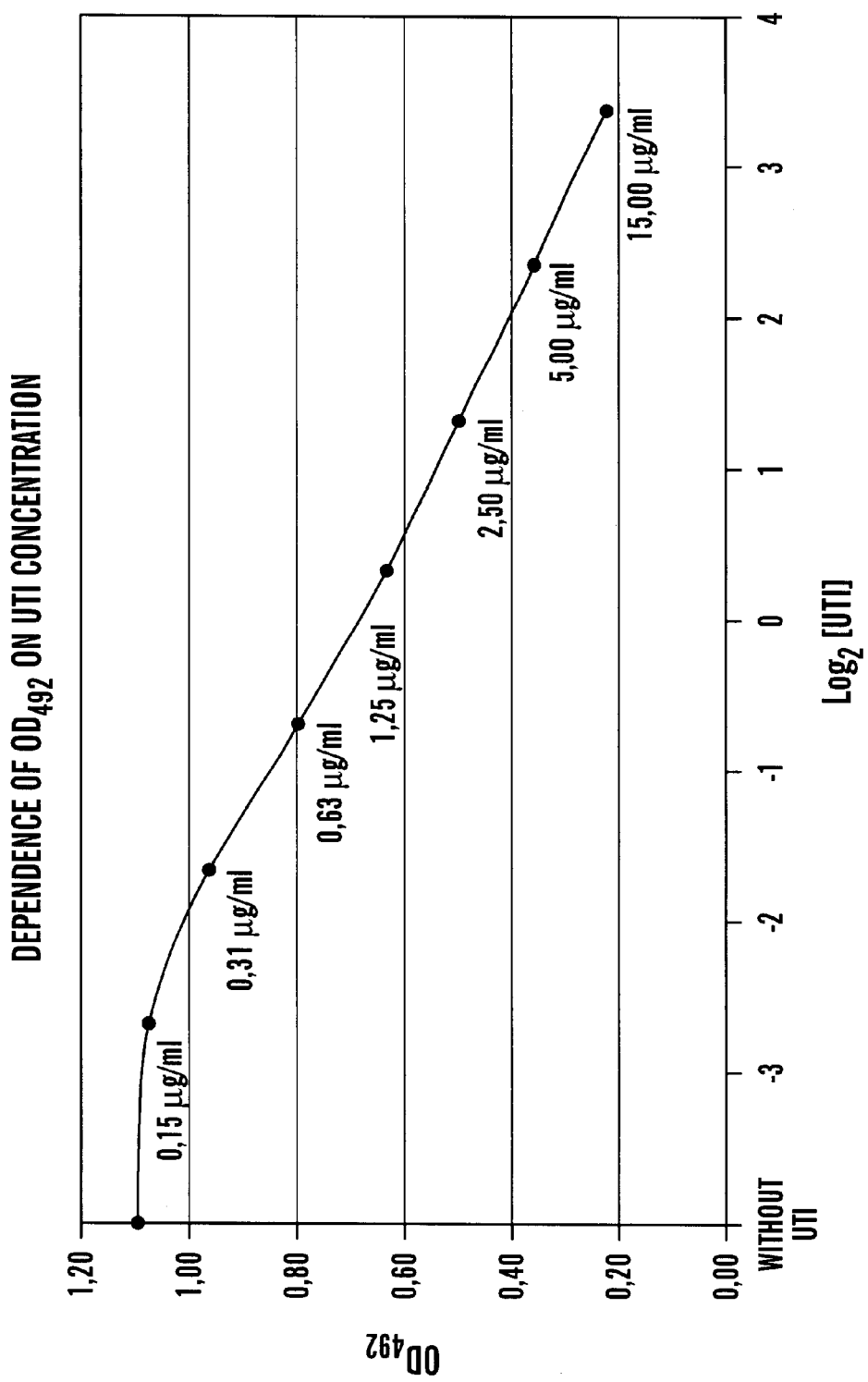

The present invention pertains to the use of the urinary trypsin inhibitor for the diagnosis of the onset of AIDS. In particular the present invention relates to the use of antibodies directed against said urinary trypsin inhibitor for the diagnosis of the onset of AIDS. In another embodiment of the invention the antibodies are provided in a kit for determining the onset of AIDS.

In the early 80's patients were observed in hospitals that had developed severe immunodeficiencies. Some of them developed unusual opportunistic infections while others have been found to suffer from Kaposi's sarcoma, a hitherto rare skin tumor. An immunologic evaluation of these patients showed a marked deficiency of the cellular immune function and a selective decrease of the number of T4 (helper) cells, a subpopulation of T cells that mediate the cellular immune response. This condition with all of its accompanied symptoms was termed "Acquired Immune Deficiency Syndrome" (AIDS). The disease itself was subsequently found to be caused by a pathogenic retrovirus called human immunodeficiency virus (HIV-virus).

Soon after HIV was found to be the origin of AIDS it was observed that this virus was in particular cytopathic for T4 cells. It was therefore hypothesized that the immunological abnormalities in AIDS resulted at least in part from a progressive depletion of T4 cells due to their infection and destruction by HIV.

From the clinical point of view the "disease" AIDS is defined as the presence of a reliably diagnosed disease at least moderately indicative of cellular immune deficiency with the absence of known underlying immune deficiency and of any other reduced resistance reported to be associated with the disease, such as e.g. immunosuppressive therapy or lymphoreticular malignancy.

The disease AIDS, that is the last stage of a slowly but constantly progressing decline of the body's normal constitution, is preceded by a variety of diseases that are generically designated as "predromal AIDS". Such disorders include ARC (Aids Related Complex) which state of disease is considered to be highly predictive of the development of subsequent AIDS. ARC includes the symptoms of e.g. having fever for more than 3 months, exhibiting a loss of weight by more than 10%, suffering from diarrhoea and showing a reduced number of T4 cells. This state of disease is known to eventually develop into the so called LAIDS (Lesser AIDS) which state is characterized by the development of oral candidasis, herpes zoster, idiopathic thrombocytopenia and other diseases that are not lethal, do, however, indicate immune suppression.

Another predictive symptom for the prospective development of AIDS is the so called LAS (lymphadenopathy syndrome), which is identified by the presence of at least three or more lymph nodes outside of the regio inguinals having a diameter of more that 1 cm.

Yet, another indication for the coming development of AIDS is the ADC symptoms (AIDS dementia complex) which is seen in the increasing number of detrimental influences on brain activity.

With the progress of molecular biology and cell biology techniques the determination of various antigenic determinants of the HIV virus itself has become possible. To this end, antibodies have been prepared with which the presence of the virus in the blood of a patient can be detected. With these tests it is, however, merely possible to determine the presence or absence of an HIV infection while the imminent manifestation of the disease as such can not reliably be predicted thereby. Hence, due to the complex picture of the predromal disease states mentioned above it is often difficult for the physician to determine whether the patient is going to develop AIDS or not within the next time.

Consequently, there exists a need in the art for a reliable and quick diagnostic tool to reliably predict the onset of the disease.

The development of an HIV infection in the human body is in general determined by two interacting factors. The unique property of HIV to weaken the infected individual's immune system and the immune response of the host against the invader, which develops along with the infection's progress.

Prior to the development of the profound immunodeficiency status the immune system still performs its task to a certain extent producing particular molecules that may be detected in the infected individual long before the various conditions described above are perceived. It was therefore considered to use such molecules for the determination of the disease.

Molecules, which are presently used for this purpose, are e.g. β-microglobulin or neopterin. The use of these compounds for the determination of the disease suffers, however, from the fact that they are not particularly specific for an HIV infection and that they have to be prepared from blood samples in a complicated manner, which impedes the procedure of diagnosis. Further, the increase in the amount of those molecules in body fluids can only be determined at a stage at which other immune system parameters and virological assays already clearly indicate the development of AIDS.

Therefore, the problem underlying the present invention is to provide a novel diagnostic tool for predicting the onset of AIDS already at an early developmental stage of the disease, preferably already during predromal AIDS conditions.

The above problem has been solved by using a particular compound to be found in body fluids, the urinary trypsin inhibitor, as a diagnostic tool, and identifying its amount in said body fluids.

During the extensive experiments leading to the present invention it has been found that the amount of urinary trypsin inhibitor (UTI), which may ordinarily be present in a healthy person in the urine in an amount of up to about 3 μg/ml is markedly increased in patients suffering from an HIV infection in whom the disease is just about to develop.

Thus, according to the present invention there is provided the use of UTI in the diagnosis of the onset of AIDS, wherein the amount of UTI in a body fluid sample of an AIDS patient is determined, which body fluid may be blood or preferably urine. If the amount exceeds a certain level, in the urine 3 μg/ml, this may be taken as a reliable signal that this patient will develop the disease.

The amount of UTI in a body fluid may be determined according to methods known in the art, such as by means of antibodies, that may be polyclonal or monoclonal antibodies or an antibody containing serum. Other methods of UTI determination include measurement of the antitryptic activity or antichymotryptic activity in the sample.

The present invention also provides a kit for carrying out the determination of UTI-level in a body fluid sample, providing all the necessary ingredients and buffers for performing the assay.

In the figures,

FIG. 1 is a standard curve showing the dependency of the extinction at 492 nm on the UTI concentration During the studies leading to the present invention the manifestation of many proteinase inhibitors and the dependency of their levels on tumoral processes in a body suffering from an immunodeficiency condition was examined. One of the blood plasma inhibitors is the inter-α-trypsin inhibitor (ITI), a protein the function of which has not yet been fully elucidated. ITI is a glycoprotein with a molecular weight of about 240 kDa that is synthesized in the liver. Its concentration in blood is about 450 µg/ml.

Immunologically affixed to ITI there has been found an inhibitor having a lower molecular weight. This specific inhibitor represents a fragment of the ITI light chain containing a large number of bisulfide links which determine its acid-stability. Due to the fact that in certain pathologic conditions this inhibitor is secreted from blood into the urine said molecule is termed urinary trypsin inhibitor (UTI).

UTI is an acidic glycoprotein with a molecular weight of about 44 kDa. About 30% of its mass is comprised by two major carbohydrate chains. The molecular weight of UTI, without carbohydrates is about 30 kDa. In terms of its tertiary structure, UTI is a two-domain molecule, even though it is comprised of only one polypeptide chain. A structural homology has been noticed between both domains and also to the main pancreatic proteinase inhibitor (MPPI), present in organs of cattle. This essentially also applies to the UTI trypsin-binding domain and to its chymotrypsin-binding domain, in the region of reactive centers.

The structural homology to MPPI allows to correlate UTI to the "Kunin" inhibitors. Due to the fact that both domains of UTI are homologous to the MPPI, this polypeptide is sometimes called "Bi-Kunin". The UTI's property of inactivating elastase and neutrophilic granulocytes G cathepsin gave rise to the hypothesis that it might exhibit an anti-inflammatory effect.

On the other hand, already in 1974 a particular protein termed EDC-1 (mol. weight=27 kDa) was isolated from urine of a patient suffering from acute myeloid leucosis. In most of the oncological patients examined so far the level of EDC-1 in urine was found to correspond to the clinical progress of the disease. It decreases significantly before the appearance of clinical signs of remission and increases prior to a clinical relapse.

The analysis of the EDC-1 amino acid sequence has shown that its N-terminal sequence generally corresponds to that of UTI while the C-terminal sequences differ. It was sometimes believed that EDC-1 and UTI may emerge by lysis of various peptide links in ITI.

Meanwhile, a potential mechanism for the increase of EDC-1's content in oncological patients has been proposed. At first stages of tumoral growth the tumor-associated proteolytic activity induces an enhanced formation of α-1-proteinase inhibitor in the host, which is substantially inactivated by the tumor's proteinases. It is only in the second turn that the tumor-associated proteinases decompose the plasma ITI until EDC-1 is formed. As a result, the concentration of EDC-1 in the serum increases while the concentration of ITI decreases.

In urine and blood serum of patients suffering from different carcinomas, such as e.g. carcinoma of the stomach, the esophagus or of the large intestine, an increased level of UTI has been noticed, which level is in correlation with the progress of the disease. After a successful application of a chemotherapy the level of UTI was found to be decreased.

Moreover, in a healthy kidney UTI has been discovered in the cytoplasma of proximal canal epithelial cells, which suggests its secretion into the urine by those cells. UTI has not been discovered in glomerules, distal canals or vascular walls. Moreover, also interstices did not contain UTI, while the tissue surrounding the tumor showed a level of UTI just like in a healthy kidney. It was, therefore, suggested that cancer cells obviously do not produce UTI.

According to the present invention the increase of the UTI level in body fluids, such like blood or, more preferably urine, may now be utilized for determining the onset of the development of diseases associated with AIDS or, more preferably predromal AIDS. In an HIV-infected patient, in whom the HIV virus is presently dormant and who does not suffer from the syndromes associated with AIDS the level of UTI in the urine is in the normal range of up to 3 µg/ml like in normal healthy people. However, when the diseases making up the syndrome are about to emerge due to the patient's immune system being weakened to an extent such that it may no longer defeat "normal" bacteriological, viral or oncological occurrences in the body so that the syndrome is starting to emerge the level of UTI in urine markedly exceeds the normal level of up to 3 µg/ml.

This increase of UTI-level, measurable long before the symptoms of the diseases associated with the syndrome are noticeable, may be taken as an indication of the onset of the development of AIDS. This knowledge will allow the physician to start with an appropriate treatment of the patient before the respective person will effectively fall ill.

In addition by measuring the amount of UTI during a treatment of a patient with drugs, such as anti-HIV drugs or drugs specifically directed against the particular disease the patient has acquired, e.g. candidasis, the efficacy of said drug in an AIDS patient may be easily monitored. Consequently, when e.g. applying drugs, such as AZT or the so called "triple therapy", to a patient suffering from diseases associated with AIDS the decline of the disease may be monitored by determining the UTI level in the patient.

Moreover, the present invention also provides for the advantage that due to the possibility to monitor and HIV-infected person for the onset of the disease the amount of drugs administered to said patient before AIDS breaks out anyway may be reduced, so that the immense costs involved in such a therapy may be saved and in addition the possibility of creating resistance in the virus will be reduced as well.

Since the assay may also be carried out on a biological material easily available, i.e. urine, the assay is easy to perform. No skilled person, such as a physician or a medical technician taking the blood is necessary.

The present invention also provides for a kit to perform the assay. The kit may have e.g. simply the form of a strip on which polyclonal or monoclonal antibodies or an antibody containing serum directed against UTI have been immobilized. Thus, a sample of a biological material is simply brought in contact with the strip and a solution containing an antibody against UTI is subsequently contacted with the strip to form a sandwich with the UTI molecule. The sandwich may then be visualized by ordinary means such as e.g. applying an antibody directed to the constant part of the antibody and being linked to a marker, such as e.g. a dye, horse raddish peroxidase etc.

It will be appreciated that the skilled person will, based on his own knowledge, design the kit according to the particular needs, such as an ELISA and others. Hence in order to provide for an accurate reading of the amount of UTI present in a sample the person skilled in the art will consider the use of a corresponding apparatus, such as e.g. a photometer. In addition it will also be appreciated that techniques for raising polyclonal or monoclonal antibodies against UTI are well within the ordinary skill.

Depending on the sort of kit provided the affected person may well perform the assay at home for a general indication with e.g. dyes indicating a particular UTI content. In addition the UTI level may also be accurately determined in a laboratory with e.g. using a photometer.

EXAMPLES

Example 1

Determination of UTI via antibodies

To detect the UTI, the following procedure was used: Three monoclonal antibodies, M2, B6, P1 were raised against UTI in a manner known per se and examined in the presence of the trypsin binding domain for their binding capacity. The M2 antibody was shown to have the highest affinity for this domain. On the basis of the mab M2, a competitive ELISA of UTI concentration in urine has been set up.

The methodology that was used to detect UTI with a view of determining its value in predicting the progress of HIV infection at different stages of the disease, has revealed the following:

Results

Groups of Patients

Seventeen HIV-1-infected patients and 30 healthy volunteers were examined; 4 patients had no clinical symptoms; 8 patients had different opportunistic infections, and 5 patients had already developed AIDS.

Materials and Methods

UTI ELISA (mab to UTI: secreting hybridoma were derived from a fusion of non-secreting mouse myeloma cells (clone P3 O1) with spleen cells of BALB/c mice that have been immunized with human UTI) level in urine, residual nitrogen and creatinin concentrations and a number of immunological parameter's (CD4, CD8, CD16, B-lymphocytes, HLA-DR), p24 concentration were tested.

The preparation of urinary protein concentrates:

1. Collection of urine (preferably, the morning portion); then treatment with acetone (5 ml of urine+10 ml of acetone cooled down to +4° C.);

2. The acetone precipitation of urinary proteins may be kept at +4° C. for one month.

3. Spinning-down of protein precipitates (1.000 g, 10 min.).

4. Preparation of suspension of the precipitates obtained (precipitate +2,5 ml 0,05 M buffer, pH 7,8 the precipitate is triturated with a glass rod) the concentration and depigmentation of the urine.

5. The undissolved precipitate is centrifuged.

6. The supernatant thus obtained is used for the determination of the UTI.

ELISA-Test

1. The UTI solution is adsorbed on a plate having 96-wells for one night at a temperature of 4° C.;

2. The plate is rinsed with water and knocked out;

3. The filling of vacant binding-sites with albumin (in each well +200 µl of 1% albumin solution in 0,05 M phosphate buffer, pH 7,4 for one-hour incubation;

4. The plate is rinsed with water and knocked out.

5. The titration into the plate's well of: (a) urine specimen (see point 6 above); (b) the standard UTI solution for the calibration curve; and (c) the control sample with the known UTI content; thereto the solution of the UTI monoclonal antibodies conjugate with horse-radish peroxidase is added and one-hour incubation; the binding of UTI from the sample and that adsorbed on the plate with the antibodies.

6. The plate is rinsed with the buffer (with 0,1% albumin and Tween-20), and with water, and knocked out.

7. Development: addition of the substrate (ortho-phenylene-diamine in the citrate-phosphate buffer); incubating for 10 minutes.

8. The stopping of the reaction: +10% sulphuric acid.

9. The measurement of optical density with an ELISA-reader at 492 nm.

10. Drawing a calibration curve with known amounts of UTI; the standard curve was constructed using 2-fold dilution of UTI in the wells of the microtiter plate; the linear segment of the standard curve is to cover the working concentration range (see FIG. 1);

11. Determination of the UTI concentration of the specimen therefrom.

In order to determine the UTI concentration in blood, the following equipment may be used:

1. A 80-chanel pipette, 40×200 µl.

2. An Eppendorf centrifuge for test-tubes (microfuge).

3. An ELISA-reader with a filter for 492 nm for plates.

4. Plates for the agents.

5. The measuring of the UTI activity, in addition to concentration, would require a photometer with a 405-nm filter.

6. A washer.

Example 2

Quantitative ATA determination

The urine sample was obtained as described in example 1.

Reagents used:

1) Trypsin concentrate: 1 mg trypsin was dissolved in 1 ml of 0.0025 M HCl with 0.1 M $CaCl_2$; the solution may be stored at 4° C. up to 10 days;

2) working trypsin solution; dilute trypsin concentrate 50 times by 0.0025 M HCl with 0.1 M $CaCl_2$;

3) 0.2 M TRIS-HCl pH 7.8–8.0;

4) BAPNA concentrate (p-nitroanilide N-benzoyl-DL-arginine); dissolve 11.4 mg BAPNA in 6 ml dehydrated DMSO; store in darkness;

5) BAPNA working solution; dilute BAPNA concentrate with distilled water in a ratio of 1:2;

ATA measurements in the urine sample 1) add 40 µl of trypsin working solution and 2–80 µl of the sample to be tested into a spectrophotometer cuvette;

2) add 0.2 M TRIS-HCl, pH 7,8–8,0 for a total volume up to 160 µl;

3) mix solution and incubate for 5 min at 37° C.;

4) add 40 µl of BAPNA working solution;

5) mix solution and measure the initial optical density ($A_1$) at 405 or 410 nm in the spectrophotometer;

6) incubate the solution for 30 min at 37° C.;

7) mix solution and measure the final optical density ($A_2$) at 405 or 410 nm in the spectrophotometer.

Processing of the results obtained

The quantity of ATA is calculated with the following formulae:

$$ATA = \epsilon(B_2 - B_1 - A_2 + A_1)/(t\,V),$$

wherein $A_1$ und $A_2$ are the initial and final optical density in the presence of a tested sample, $B_1$ and $B_2$ are the initial and final optical density in the absence of the sample, V is the volume of the urine sample added, t is the reaction time and $\epsilon$ is a tabulated extinction coefficient of p-nitroaniline in dependence of the wavelength used and the total solution volume.

The most accurate results are obtained if $$0.4\,(B_2-B_1) < A_2 - A_1 < 0.6\,(B_2-B_1)$$

What is claimed is:

1. A method for diagnosing the onset of AIDS in a subject comprising:
   collecting a sample of biological fluid from the subject;
   contacting the sample of biological fluid with an antibody which binds to urinary trypsin inhibitor under immunological reaction conditions; and
   determining the concentration of urinary trypsin inhibitor in the biological sample.

2. The method according to claim 1, wherein the biological sample is blood or urine.

3. The method according to claim 1, wherein the antibody is selected from the group consisting of a polyclonal antibody, a monoclonal antibody, and antibody-containing sera.

4. The method according to claim 1, wherein the antibody is immobilized on a solid surface, whereby said contacting will immobilize any urinary trypsin inhibitor in the biological sample, said method further comprising:
   labeling, after said contacting and before said determining, any urinary trypsin inhibitor which is immobilized on the solid surface with a labeled antibody which binds to the urinary trypsin inhibitor under immunological reaction conditions.

5. The method according to claim 4, wherein the label is selected from the group consisting of a dye, an enzyme, a fluorescent marker, and a radioactive marker.

6. The method according to claim 5, wherein said method is carried out in an ELISA assay.

7. A method for diagnosing the onset of AIDS in a subject comprising:
   collecting a sample of biological fluid from the subject;
   measuring the level of antitryptic activity in the sample; and
   determining the concentration of urinary trypsin inhibitor in the sample based on the level of antitryptic activity in the sample.

8. A method for diagnosing the onset of AIDS in a subject comprising:
   collecting a sample of biological fluid from the subject;
   measuring the level of antichymotrypsin activity in the sample; and
   determining the concentration of urinary trypsin inhibitor in the sample based on the level of antichymotrypsin activity in the sample.

9. A method of determining the efficacy of an anti-HIV drug comprising:
   collecting a sample of biological fluid from a subject receiving one or more anti-HIV drugs;
   contacting the sample of biological fluid with an antibody which binds to urinary trypsin inhibitor under immunological reaction conditions;
   determining the concentration of urinary trypsin inhibitor in the biological sample; and
   comparing the levels of urinary trypsin inhibitor measured at different times during the administration of an anti-HIV drug.

10. The method according to claim 9, wherein the biological sample is blood or urine.

11. The method according to claim 9, wherein the antibody is selected from the group consisting of a polyclonal antibody, a monoclonal antibody, and antibody-containing sera.

12. The method according to claim 9, wherein the antibody is immobilized on a solid surface, whereby said contacting will immobilize any urinary trypsin inhibitor in the biological sample, said method further comprising:
    labeling, after said contacting and before said determining, any urinary trypsin inhibitor which is immobilized on the solid surface with a labeled antibody which binds to the urinary trypsin inhibitor under immunological reaction conditions.

13. The method according to claim 12, wherein the label is selected from the group consisting of a dye, an enzyme, a fluorescent marker, and a radioactive marker.

14. The method according to claim 13, wherein the method is carried out in an ELISA assay.

15. A kit for the diagnosis of urinary trypsin inhibitor as an indicator for the onset of AIDS, said kit comprising:
    an antibody which binds to urinary trypsin inhibitor under immunological reaction conditions.

16. The kit according to claim 15 further comprising:
    a solid support suitable for immobilizing the antibody and
    a labeled antibody which binds to the urinary trypsin inhibitor under immunological reaction conditions.

17. The kit according to claim 16, wherein the label is selected from the group consisting of a dye, an enzyme, a fluorescent marker, and a radioactive marker.

18. The kit according to claim 16, wherein the antibodies are selected from the group consisting of a polyclonal antibody, a monoclonal antibody, and an antibody-containing sera.

* * * * *